United States Patent [19]

Newton

[11] Patent Number: 5,780,393
[45] Date of Patent: Jul. 14, 1998

[54] HERBICIDAL ISOXAZOLE AND ISOTHIAZOLE-5-CARBOXAMIDES

[75] Inventor: Trevor W. Newton, Schwabenheim, Germany

[73] Assignee: American Cyanamid Company, Madison, N.J.

[21] Appl. No.: 702,779

[22] Filed: Aug. 23, 1996

Related U.S. Application Data

[60] Provisional application No. 60/002,728, Aug. 24, 1995.
[51] Int. Cl.⁶ .................. A01N 43/74; C07D 261/18
[52] U.S. Cl. .................. 504/271; 548/248; 546/272.1; 504/252
[58] Field of Search .................. 548/248; 514/378; 504/271

[56] References Cited

U.S. PATENT DOCUMENTS

| | | | |
|---|---|---|---|
| 3,668,215 | 6/1972 | Plumpe et al. | 260/370 H |
| 3,755,587 | 8/1973 | Plumpe et al. | 424/267 |
| 3,912,756 | 10/1975 | Wolff et al. | 260/326.13 R |
| 5,039,694 | 8/1991 | Suzuki et al. | 514/406 |
| 5,080,708 | 1/1992 | Freund et al. | 71/88 |
| 5,201,932 | 4/1993 | Maywald et al. | 504/271 |
| 5,240,951 | 8/1993 | Shimotori et al. | 514/372 |

FOREIGN PATENT DOCUMENTS

| | | | |
|---|---|---|---|
| 41 08 183 A1 | 3/1991 | Denmark | C07D 261/18 |
| 0 313 091 | 10/1988 | European Pat. Off. | C07D 277/56 |
| 0 428 434 A3 | 11/1990 | European Pat. Off. | C07D 211/14 |
| 0 669 326 A1 | 2/1995 | European Pat. Off. | C07D 261/18 |
| 3618004 | 12/1987 | Germany . | |
| 45007054 | 3/1970 | Japan . | |
| A 54044686 | 4/1979 | Japan . | |
| 2 284 600 A | 11/1994 | United Kingdom . | |

OTHER PUBLICATIONS

Chem. Abstr. 175401n, vol. 91, No. 21 (1979).
Chem. Abstr. 132705e, vol. 72, No. 25 (1970).
Musant C. Fabrini L. *Gazetta Chimica Italiana*, vol. 81, pp. 117–124 (1951).
Plumpe, H. *Arzneimittel—Forschung*, vol. 24, No. 3A, pp. 363–374 (1974).

*Primary Examiner*—Joseph McKane
*Assistant Examiner*—Laura R. C. Lutz
*Attorney, Agent, or Firm*—Joseph M. Mazzarese

[57] ABSTRACT

There are provided isoxazole- and isothiazole-5-carboxamide compounds of formula I

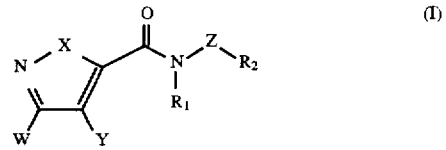

which are useful for the control of undesirable monocotyledenous and dicotyledenous plant species in the presence of crops such as cereal and leguminous crops. Also provided are herbicidal compositions and methods of using same.

20 Claims, No Drawings

HERBICIDAL ISOXAZOLE AND ISOTHIAZOLE-5-CARBOXAMIDES

This application claims the benefit of copending prior U.S. Provisional Application Ser. No. 60/002,728 filed on Aug. 24, 1995.

BACKGROUND OF THE INVENTION

This invention relates to isoxazole- and isothiazole-5-carboxylic acid amide compounds, the preparation of said compounds, herbicidal compositions containing said compounds, and a method of controlling undesired plant growth therewith.

Amides of isoxazole- and isothiazole-5-carboxylic acids are well known in the chemical literature. Several N-aralkyl and N-heteroaralkyl amides of said acids have been reported to have useful pharmaceutical and agrochemical applications; for example, U.S. Pat. No. 3,912,756 describes the preparation of N-(4-carboxyalkoxy)phenylalkylenyl isoxazole-5-carboxamides as hypolipemics; and U.S. Pat. No. 5,039,694 describes the preparation and fungicidal activity of N-(substituted heterocyclyl-methyl)isoxazole-5-carboxamides.

Further, the herbicidal activity of isoxazole-5-carboxamides which are substituted in the 4-position by a carbonyl or carboxyl group is described in U.S. Pat. No. 5,080,708 and U.S. Pat. No. 5,201,932. In U.S. Pat. No. 5,080,708, the benzyl amide of a 3-alkyl-isoxazole-5-carboxylic acid, which is unsubstituted in the 4-position, is cited as an intermediate in the preparation of herbicidal compounds. However, there is no indication that said compound, lacking a 4-substituent, may show herbicidal activity.

Therefore, it is an object of this invention to provide herbicidal isoxazole- and isothiazole-5-carboxamide compounds.

It is another object of this invention to provide herbicidal compositions and methods utilizing said heterocyclyl-5-carboxamide compounds.

It is a feature of this invention that said herbicidal compositions may be used to selectively control undesirable weed species in the presence of a crop, such as a cereal crop or a leguminous crop.

These and other objects and features of the invention will become apparent from the detailed description set forth below.

SUMMARY OF THE INVENTION

The present invention provides herbicidal isoxazole- and isothiazole-5-carboxamide compounds of formula I

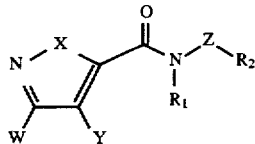

(I)

wherein X represents an oxygen or sulfur atom;
W represents an optionally substituted alkyl, alkenyl, cycloalkyl, dialkylamino, aryl, heteroaryl or aralkyl group;
Y represents a hydrogen atom, a halogen atom, or an optionally substituted alkyl group;
$R_1$ represents a hydrogen atom, an optionally substituted alkyl group, or an optionally substituted acyl group;
Z represents an optionally substituted $C_1$–$C_4$alkylene group with the proviso that when $R_1$ is hydrogen and Z is methylene, then the optional substituent does not represent cyano, thiocarbamoyl or thiocarbamoylacyl; and
$R_2$ represents an optionally substituted aryl or heteroaryl group with the proviso that when X represents a sulfur atom then $R_2$ does not represent a furyl group or a phenyl group optionally substituted with halogen and with the further proviso that when Z represents an unsubstituted methylene group, then $R_2$ does not represent an unsubstituted phenyl group; or
the N-oxides thereof; or
the optical isomers thereof.

There are further provided methods for the control of undesirable monocotyledenous and dicotyledenous plant species in the presence of a crop, such as a cereal crop or leguminous crop. Herbicidal compositions and methods of using same are also provided.

DETAILED DESCRIPTION OF THE INVENTION

Crop production can be reduced by as much as 30% to 60% by the presence of persistent and pestiferous weed species. Compounds which demonstrate effective control over a broad spectrum of annual and perennial monocotyledenous and dicotyledenous weeds in the presence of a crop, while commensurately demonstrating selective tolerance toward that crop, are of great interest in agricultural practice and modern pest management programs.

It has now been found that a broad spectrum of grass weeds and broad-leafed weeds may be effectively controlled in the presence of a crop, such as a cereal crop or leguminous crop, with little or no phytotoxic injury to said crop by the preemergence or postemergence application of an isoxazole- or isothiazole-5-carboxamide compound of formula I

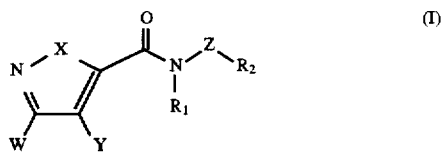

(I)

wherein X represents an oxygen or sulfur atom;
W represents an optionally substituted alkyl, alkenyl, cycloalkyl, dialkylamino, aryl, heteroaryl or aralkyl group;
Y represents a hydrogen atom, a halogen atom, or an optionally substituted alkyl group;
$R_1$ represents a hydrogen atom, an optionally substituted alkyl group, or an optionally substituted acyl group;
Z represents an optionally substituted $C_1$–$C_4$alkylene group; and
$R_2$ represents an optionally substituted aryl or heteroaryl group; or
the N-oxides thereof; or
the optical isomers thereof.

Preferably, W represents an optionally substituted alkyl, cycloalkyl, alkenyl, dialkylamino, phenyl, pyridyl, furyl or thienyl group.

More preferably, W represents a branched $C_3$–$C_6$alkyl group or a phenyl group which is optionally substituted with one or two substituents independently selected from halogen, $C_1$–$C_4$alkyl, $C_1$–$C_4$alkoxy or $C_1$–$C_4$haloalkyl. Most preferably, W represents a t-butyl group or a phenyl group.

Preferably, Y and $R_1$ each represent a hydrogen atom.

A preferred optionally substituted alkylene group Z has the formula —CH($R_3$)—, wherein $R_3$ represents a hydrogen atom or an optionally substituted $C_1$–$C_2$alkyl group, more preferably a methyl group.

The group $R_2$ preferably represents either phenyl optionally substituted by 1 or 2 moieties independently selected from halogen and $C_1$–$C_4$alkyl, or furyl, pyridyl, thienyl or benzothienyl. More preferably, $R_2$ represents a phenyl or thienyl group.

In the specification and claims the term alkyl group designates an alkyl group which may be linear or branched and may suitably contain 1 to 10, preferably 1 to 6, carbon atoms. Examples of such alkyl groups are methyl, ethyl, i-propyl, n-butyl, i-butyl, s-butyl, t-butyl, n-pentyl, i-pentyl, s-pentyl, neopentyl and the like. Similarly, an alkenyl group may suitably contain 2 to 8 carbon atoms; a cycloalkyl group may have from 3 to 8, preferably 3 to 6, carbon atoms, more preferably 5 or 6 carbon atoms. The term, an acyl group, as used in the specification and claims designates a carbonyl group attached to an optionally substituted alkyl, aryl or heteroaryl group and suitably contains 2 to 8 carbon atoms.

An aralkyl group designates an alkyl group, defined as above, substituted by an aryl group. An aryl group designates an optionally substituted phenyl or naphthyl group. A heteroaralkyl group designates an alkyl group, defined as above, substituted by a heteroaryl group. A heteroaryl group designates a mono- or polycyclic ring system consisting of 5- or 6-membered aromatic rings containing one or more sulfur or nitrogen or oxygen atoms or combinations thereof. Any or all of the constituent groups may be optionally substituted.

The optional substituent groups may be any of those customarily employed in the development of pesticidal compounds, or the modification of such compounds to influence their structure/activity, persistence, penetration or other property. Optional substituent groups designated above in the terms: an optionally substituted alkyl, alkenyl or cycloalkyl group, including the alkyl portions of aralkyl, heteroaralkyl or acyl groups, include halogen, especially fluorine, chlorine or bromine atoms, phenyl, nitro, cyano, hydroxyl, $C_1$–$C_4$alkoxy, $C_1$–$C_4$alkyl, $C_1$–$C_4$haloalkoxy, ($C_1$–$C_4$alkoxy)- carbonyl, amino, alkyl- and phenyl-sulfinyl, -sulphenyl and -sulfonyl groups, mono- and di(C1–C4alkyl) amino groups and the like, preferably halogen.

Optional substituent groups defined above in the terms: an optionally substituted aryl or heteroaryl group, including aryl and heteroaryl parts of aralkyl, heteroaralkyl and acyl groups, may include halogen, especially fluorine, chlorine and bromine atoms, nitro, cyano, amino, hydroxyl, $C_1$–$C_4$alkyl, $C_1$–$C_4$haloalkyl, especially $CF_3$, $C_1$–$C_4$alkoxy, $C_1$–$C_4$haloalkoxy groups and the like.

Included in the scope of the present invention are all possible enantiomers and diastereoisomers of the compounds of the formula I having one or more optically active centers, and also the N-oxides of the isoxazole or isothiazole ring nitrogen atom.

Particularly interesting herbicidal activity has been found in the (S)-isomers of those formula I compounds wherein Z represents the group —*CH($R_3$)—, and *C designates an asymetric center.

Among the specific compounds of the invention which may be represented by formula I are compounds such as:

(S)-3-t-Butyl-isoxazole-5-carboxylic acid (1-phenylethyl) amide;

(S)-3-t-Butyl-isoxazole-5-carboxylic acid (1-thien-2-ylethyl)amide;

(R/S)-3-(2-Fluorophenyl)isothiazole-5-carboxylic acid (1-thien-2-ylethyl)amide;

(R/S)-3-t-Butyl-isoxazole-5-carboxylic acid (1-thien-2-ylethyl)amide;

(S)-3-Phenyl-isoxazole-5-carboxylic acid (1-phenylethyl) amide;

(R/S)-3-Phenyl-isoxazole-5-carboxylic acid (1-thien-2-ylethyl)amide;

(R/S)-3-Styryl-isoxazole-5-carboxylic acid (1-thien-2-ylethyl)amide;

(R/S)-3-Cyclohexyl-isoxazole-5-carboxylic acid (1-thien-2-ylethyl)amide;

(R/S)-3-Dimethylamino-isoxazole-5-carboxylic acid (1-thien-2-ylethyl)amide;

(R/S)-3-(2'-Pyridyl)isoxazole-5-carboxylic acid (1-thien-2-ylethyl)amide;

(R/S)-3-(2'-Thienyl)isoxazole-5-carboxylic acid (1-thien-2-ylethyl)amide;

(R/S)-3-(4'-Methylphenyl)isoxazole-5-carboxylic acid (1-thien-2-ylethyl)amide;

(R/S)-3-(4'-Methoxyphenyl)isoxazole-5-carboxylic acid (1-thien-2-ylethyl)amide;

(R/S)-3-(2',4'-Difluorophenyl)isoxazole-5-carboxylic acid (1-thien-2-ylethyl)amide;

(R/S)-3-Benzyl-isoxazole-5-carboxylic acid (1-thien-2-ylethyl)amide;

(R/S)-3-t-Butyl-4-chloro-isoxazole-5-carboxylic acid (1-thien-2-ylethyl)amide;

(R/S)-3-t-Butyl-4-methyl-isoxazole-5-carboxylic acid (1-thien-2-ylethyl)amide;

(R/S)-3-t-Butyl-isoxazole-5-carboxylic acid N-methyl,N-(1-thien-2-ylethyl)amide;

(R/S)-3-t-Butyl-isoxazole-5-carboxylic acid N-acetyl,N-(1-thien-2-ylethyl)amide;

3-t-Butyl-isoxazole-5-carboxylic acid (thien-2-yl-methyl) amide;

(R/S)-3-t-Butyl-isoxazole-5-carboxylic acid (1-(4'-chlorophenyl)ethyl)amide;

(R/S)-3-t-Butyl-isoxazole-5-carboxylic acid (1-(4'-methylphenyl)ethyl)amide;

(R/S)-3-t-Butyl-isoxazole-5-carboxylic acid (1-furan-2-ylethyl)amide;

(R/S)-3-t-Butyl-isoxazole-5-carboxylic acid (1-(2'-pyridyl) ethyl)amide;

(R/S)-3-t-Butyl-isoxazole-5-carboxylic acid (1-thien-3-ylethyl)amide;

(R/S)-3-t-Butyl-isoxazole-5-carboxylic acid (1-(2'-benzothienyl)ethyl)amide and the like.

The compounds of the invention may be oils, gums, or, predominantly, crystalline solid materials. Said compounds demonstrate valuable herbicidal properties and may be used in agriculture or related fields for the control of a wide spectrum of undesired monocotyledenous and dicotyledenous plant species. Further, compounds of formula I demonstrate good herbicidal activity within a wide concentration range and advantageously, may be used in crop production, such as cereal crop production or leguminous crop production without causing an unacceptable phytotoxic effect on said crops.

The present invention also provides a process for the preparation of a compound of formula I which comprises reacting a compound of formula II

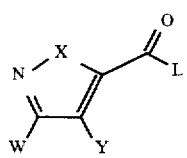

(II)

wherein W, X and Y are as defined hereinabove for formula I and L represents a leaving group, with a compound of formula III

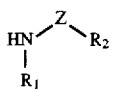

(III)

wherein Z, $R_1$ and $R_2$ are as defined hereinabove for formula I.

The leaving group L as used in the specification and claims designates a halogen atom, such as chlorine; an acyloxy group, such as acetoxy; an alkoxy group, such as a methoxy or ethoxy group; or an aryloxy group, such as a phenoxy group. Preferably, L represents a methoxy or ethoxy group.

When L represents an alkoxy group, the reaction may be carried out in an organic solvent, for example ethanol or toluene, and at a temperature range at about room temperature to the reflux temperature of the reaction mixture. The reaction is most effectively carried out under basic conditions. The basic conditions may be provided by employing an excess of the amine of formula III in the reaction, for example a two-fold excess.

Alternatively, the basic conditions may be provided by the separate inclusion of a base in the reaction mixture. The base may be any of those commonly employed in organic chemistry, for instance, a hydroxide, hydride, alkoxide, carbonate or hydrogen carbonate salt of an alkali metal or an alkaline earth metal; or an amine. A preferable base is a tertiary amine, for example triethylamine.

In another embodiment of the above process, a compound of formula I may be prepared by reacting a compound of formula II with a salt of formula IV

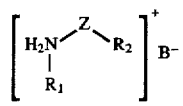

(IV)

wherein Z, $R_1$ and $R_2$ are as defined hereinabove and $B^-$ is a suitable anion, for example a chloride, bromide, iodide, sulfate or (R)-2-hydroxysuccinate, in the presence of a base. The reaction may be carried out in an organic solvent, for example ethanol or toluene, and at a temperature range of about room temperature to the reflux temperature of the reaction mixture. The base may be any of those commonly employed in organic chemistry, for instance, a hydroxide, hydride, alkoxide, carbonate or hydrogen carbonate salt of an alkali metal or an alkaline earth metal; or an amine, preferably a tertiary amine, for example triethylamine. The amount of base used may be an excess amount, for example a four-fold excess.

Many starting isoxazole- and isothiazole-5-carboxylates of formula II wherein L represents an alkoxy group are known or may be prepared by known methods, such as those described by O. Moriya et al, J. Chem. Soc., Chem. Comm., 17, (1991); R. Howe et al, J. Chem. Soc., Chem. Comm., 524, (1973), or D. Buffel et al, J. Org. Chem., 49, 2165, (1984).

The amines of formula III and the salts of formula IV are known, or may be obtained from known materials by standard synthetic techniques.

The formula I compounds of the invention are highly effective herbicidal agents. Accordingly, the invention further provides a herbicidal composition comprising a compound of formula I as defined above in association with at least one carrier Preferably there are at least two carriers, at least one of which is a surface-active agent.

A carrier, as intended for use in a composition of the invention, is any material with which the active ingredient is formulated to facilitate application, or to facilitate storage, transport or handling. A carrier may be a solid or a liquid, including a material which is normally gaseous but which has been compressed to form a liquid. Any of the carriers normally used in formulating herbicidal compositions may be used. Compositions according to the invention may contain about 0.5% to 95% by weight of active ingredient.

Suitable solid carriers include natural and synthetic clays and silicates, for example natural silicas such as diatomaceous earths; magnesium silicates, for example talcs; magnesium aluminum silicates, for example attapulgites and vermiculites; aluminum silicates, for example kaolinites, montmorillonites and micas; calcium carbonate; calcium sulfate; ammonium sulfate; synthetic hydrated silicon oxides and synthetic calcium or aluminum silicates; elements, for example carbon and sulfur; natural and synthetic resins, for example coumarone resins, polyvinyl chloride, and styrene polymers and copolymers; solid polychlorophenols; bitumen; waxes; and solid fertilizers, for example superphosphates; and the like.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane; and the like or mixtures thereof.

Agricultural compositions may be formulated and transported in a concentrated form and subsequently diluted before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface active agent.

A surface-active agent may be an emulsifying agent, a dispersing agent or a wetting agent; it may be nonionic or ionic. Examples of suitable surface-active agents include the sodium or calcium salts of polyacrylic acids and lignin sulfonic acids; the condensation products of fatty acids or aliphatic amines or amides containing at least 12 carbon atoms in the molecule with ethylene oxide or propylene oxide; fatty acid esters of glycerol, sorbitan, sucrose or pentaerythritol; condensates of these with ethylene oxide or propylene oxide; condensation products of fatty alcohol or alkyl phenols, for example p-octylphenol or p-octylcresol, with ethylene oxide or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulfate, sodium secondary alkyl sulfates, sodium salts of sulfonated castor oil, and sodium alkaryl sulfonates such as dodecylbenzene sulfonate; polymers of ethylene oxide and copolymers of ethylene oxide and propylene oxide; and the like.

The compositions of the invention may take the form of wettable powders, dusts, granules, soluble granules, solutions, emulsifiable concentrates, emulsions, suspension concentrates, microemulsions or the like.

Aqueous dispersions, emulsions, solutions and such compositions obtained by diluting a wettable powder or a concentrate according to the invention with water, are also included within the scope of the invention.

The composition of the invention may also contain other active ingredients, such as other compounds possessing herbicidal, insecticidal or fungicidal properties.

The present invention further provides a method for the control of undesirable monocotyledenous and dicotyledenous annual, perennial and aquatic plant species which comprises applying to the foliage of said plant species or to the soil or water containing seeds or other propagating organs thereof a herbicidally effective amount of an isoxazole- or isothiazole-5-carboxamide compound of formula I.

Particularly interesting control of grasses and broad-leafed weeds, both preemergence and postemergence, has been found. The selective control of said weeds in important crop species such as wheat, barley, maize, rice and soybeans has also been found.

Dosage rates for effective weed control may vary according to the prevailing conditions such as soil conditions, weather conditions, weed population and density, mode of application and the like. Dosage rates of about 0.01 kg/ha to 10 kg/ha, preferably about 0.05 kg/ha to 4.0 kg/ha offer effective weed control.

For a more clear understanding of the invention, specific examples thereof are set forth below. The invention described and claimed herein is not to be limited in scope by these merely illustrative examples. Indeed, various modifications of the invention in addition to those exemplified and described herein will become apparent to those skilled in the art from the following examples and the foregoing description. Such modifications are also intended to fall within the scope of the appended claims In the examples, the term NMR designates nuclear magnetic resonance and flash chromatography refers to column chromatography performed under moderate pressure.

EXAMPLE 1

(S)-3-t-Butyl-isoxazole-5-carboxylic acid (1-phenethyl)amide (a) Ethyl 3-t-butyl-isoxazole-5-carboxylate Hexabutyl distannoxane (16.0 mL, 31.5 mmol) is added dropwise, with cooling, to a stirred solution of ethyl propionate (13.7 mL, 126 mmol) and trimethylacetaldoximoyl chloride (8.5 g, 63 mmol, prepared according to J. N. Kim et al. J. Org. Chem., 57, 6649, 1992) in dry toluene. The mixture is stirred at room temperature for 16 h and the solvent is evaporated in vacuo. The resultant residue is purified by flash column chromatography (silica gel, hexane/ethyl acetate 8:1 v/v) to give ethyl 3-t-butyl-isoxazole-5-carboxylate (12 g, 97%) as a yellow oil, which is used in the following reaction.

(b) (S)-3-t-Butyl-isoxazole-5-carboxylic acid (1-phenethyl)amide

A solution of ethyl 3-t-butyl-isoxazole-5-carboxylate (1.58 g, 8 mmol) and (S)-1-phenethylamine (2.91 g, 24 mmol) in absolute ethanol is refluxed for 7 days and concentrated in vacuo to give a residue. The residue is purified by flash column chromatography (silica gel, hexane/ethyl acetate 4:1 v/v) to give (s)-3-t-butyl-isoxazole-5-carboxylic acid (1-phenethyl)amide (1.01 g, 46%) as colorless crystals, mp 130°–131° C.

EXAMPLE 2

(S)-3-t-Butyl-isoxazole-5-carboxylic acid (1-thien-2-ylethyl)amide (a) (S)-(1-Thien-2-ylethyl)ammonium (R)-2-hydroxysuccinate (R/S)-1-(Thien-2-ylethyl)amine (381.6 g, 3.0 mol) is added dropwise to a stirred solution of D-(+)-2-hydroxysuccinic acid (402.3 g, 3.0 mol) in water at room temperature. During the addition, the temperature of the solution rises to 55°–60° C. The solution is allowed to stand at room temperature for about 16 h, during which time a crystalline precipitate forms and the precipitate is filtered off. The optical purity of the salt is determined as follows: A small quantity of the salt is treated with a 10% molar excess of sodium hydroxide in water and the aqueous solution is extracted with dichloromethane. The organic extracts are combined, dried over magnesium sulfate and concentrated in vacuo. The optical purity of the sample of free amine so generated is determined by NMR spectroscopy using a chiral shift reagent, e.g. Eu(fod)$_3$. The bulk of the salt is then recrystallized from water and the optical purity of the amine portion of the salt is redetermined by the same procedure. This process is repeated until a satisfactory optical purity is achieved. If the salt is allowed to recrystallize slowly, a ratio of 92:8 of the S-enantiomer to the R-enantiomer of the amine can be obtained after a single recrystallization. The yield of (S)-1-(thien-2-ylethyl) ammonium (R)-2-hydroxysuccinate is 195.0 g, 50% of theory, mp>300° C.

(b) (S)-3-t-Butyl-isoxazole-5-carboxylic acid (1-thien-2-ylethyl)amide

Triethylamine (3.26 g, 32 mmol) is added to a stirred suspension of (S)-1-(thien-2-ylethyl)ammonium (R)-2-hydroxysuccinate (2.30 g, 8.8 mmol) in absolute ethanol (25 mL), and the mixture is stirred at room temperature for 5 min, during which time a clear solution is formed. Ethyl 3-t-butyl-isoxazole-5-carboxylate (1.58 g, 8 mmol) is added and the mixture is refluxed for 9 days. A further small portion of triethylamine is added to the reaction mixture, and the mixture is heated at reflux temperature for another 8 h. The solvent is evaporated in vacuo to give a residue. The residue is dissolved in dichloromethane, washed with 1N hydrochloric acid, dried over anhydrous magnesium sulfate, and concentrated in vacuo to give a second residue. This second residue is purified by flash column chromatography (silica gel, hexane/ethyl acetate 4:1 v/v) to give (S)-3-t-butyl-isoxazole-5-carboxylic acid (1-thien-2-ylethyl)amide (460 mg, 20%) as colorless crystals, mp 92° C.

EXAMPLE 3

(R/S)-3-(2-Fluorophenyl)isothiazole-5-carboxylic acid (1-thien-2-ylethyl)amide (a) 5-(2-Fluorophenyl)|1,3,4|oxathiazolin-2-one Chlorocarbonyl sulfenyl chloride (11.24 g, 86 mmol) is added dropwise to a stirred suspension of 2-fluorobenzamide (10.80 g, 78 mmol) in dry toluene. The mixture is heated gradually over a period of 30 minutes to a temperature of about 80° C. (a clear solution is formed with evolution of gas), stirred for approximately 1 h at 80° C., heated to about 98° C., stirred at 98° C. for 5 h, and distilled to remove the toluene and excess chlorocarbonyl sulfenyl chloride. The resultant pot residue is redissolved in toluene, washed sequentially with water, 5% sodium bicarbonate and water, dried over anhydrous magnesium sulfate and concentrated in vacuo to give a residue. This residue is recrystallized from petroleum ether to give 5-(2-fluorophenyl)|1,3,4| oxathiazolin-2-one (13.2 g, 86%) as off-white crystals, mp 50° C.

(b) Ethyl 3-(2-fluorophenyl)isothiazole-5-carboxylate

A solution of 5-(2-fluorophenyl)|1,3,4|oxathiazolin-2-one (1.97 g, 10 mmol) and ethyl propiolate (1.96 g, 20 mmol) in p-xylene is heated at reflux temperature for 48 h, treated with a further portion of ethyl propionate, heated at reflux temperature for another 48 h, and distilled to remove the solvent. The resultant residue is purified by flash column chromatography (silica gel, toluene) to give ethyl 3-(2-fluorophenyl)isothiazole-5-carboxylate (1.0 g, 40%) as yellow crystals, mp 53°–54° C., plus ethyl 3-(2-fluorophenyl)isothiazole-4-carboxylate (0.8 g, 32%) as a yellow oil.

(c) 3-(2-Fluorophenyl)isothiazole-5-carboxylic acid

A solution of sodium hydroxide (0.17 g, 4.2 mmol) in water (4 mL) is added to a stirred solution of ethyl 3-(2-fluorophenyl)isothiazole-5-carboxylate (0.88 g, 3.5 mmol) in ethanol. The mixture is stirred for 6 h at 50° C. The ethanol is then removed by distillation and the resulting aqueous phase is washed with diethyl ether, acidified with 2N hydrochloric acid and filtered. The filtercake is dried in vacuo to give 3-(2-fluorophenyl)isothiazole-5-carboxylic acid (0.67 g, 86%) as beige crystals, mp 191°–192° C.

(d) (R/S)-3-(2-Fluorophenyl)isothiazole-5-carboxylic acid (1-thien-2-ylethyl)amide A stirred solution of 3-(2-fluorophenyl)isothiazole-5-carboxylic acid (0.67 g, 3.0 mmol) in dry tetrahydrofuran is treated with 1,1'-carbonyldiimidazole (CDI) (0.54 g, 3.3 mmol), heated at reflux temperature for 30 minutes, cooled to room temperature, treated with (R/S)-1-(thien-2-ylethyl)amine (0.57 g, 4.5 mmol), stirred for 10 minutes, treated with a solution of 1,8-diazabicyclo[5.4.0]undec-7-ene (DBU) (0.50 g, 3.3 mmol) in ethanol, heated at reflux temperature for 4.5 h, allowed to stand at room temperature overnight and distilled to remove the tetrahydrofuran. The distillation residue is dissolved in ethyl acetate, washed sequentially with 2N hydrochloric acid and water, dried over anhydrous magnesium sulfate and concentrated in vacuo to give a residue. This residue is recrystallized from toluene to yield (R/S)-3-(2-fluorophenyl)isothiazole-5-carboxylic acid (1-thien-2-ylethyl)amide (0.70 g, 70%) as beige crystals, mp 158°–159° C.

EXAMPLES 4–26

Using essentially the same procedures described in Examples 1–3 hereinabove, the following compounds are obtained and shown in Table I.

TABLE I

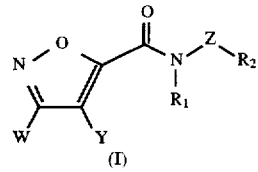

(I)

| Ex. No | W | Y | $R_1$ | $R_2$ | $R_3$ | Stereochem. | MP(°C.) |
|---|---|---|---|---|---|---|---|
| 4 | t-Butyl | H | H | 2-Thienyl | $CH_3$ | (R/S) | 94–96 |
| 5 | Phenyl | H | H | Phenyl | $CH_3$ | (S) | 173–175 |
| 6 | Phenyl | H | H | 2-Thienyl | $CH_3$ | (R/S) | 138–140 |
| 7 | Styryl | H | H | 2-Thienyl | $CH_3$ | (R/S) | |
| 8 | Cyclohexyl | H | H | 2-Thienyl | $CH_3$ | (R/S) | |
| 9 | Dimethylamino | H | H | 2-Thienyl | $CH_3$ | (R/S) | |
| 10 | 2-Pyridyl | H | H | 2-Thienyl | $CH_3$ | (R/S) | |
| 11 | 2-Thienyl | H | H | 2-Thienyl | $CH_3$ | (R/S) | |
| 12 | p-Tolyl | H | H | 2-Thienyl | $CH_3$ | (R/S) | |
| 13 | 4-Methoxyphenyl | H | H | 2-Thienyl | $CH_3$ | (R/S) | |
| 14 | 2,4-Difluorophenyl | H | H | 2-Thienyl | $CH_3$ | (R/S) | 109–110 |
| 15 | Benzyl | H | H | 2-Thienyl | $CH_3$ | (R/S) | |
| 16 | t-Butyl | Cl | H | 2-Thienyl | $CH_3$ | (R/S) | |
| 17 | t-Butyl | $CH_3$ | H | 2-Thienyl | $CH_3$ | (R/S) | |
| 18 | t-Butyl | H | $CH_3$ | 2-Thienyl | $CH_3$ | (R/S) | |
| 19 | t-Butyl | H | $CH_3CO$ | 2-Thienyl | $CH_3$ | (R/S) | |
| 20 | t-Butyl | H | H | 2-Thienyl | H | (R/S) | |
| 21 | t-Butyl | H | H | 4-Chlorophenyl | $CH_3$ | (R/S) | |
| 22 | t-Butyl | H | H | p-Tolyl | $CH_3$ | (R/S) | |
| 23 | t-Butyl | H | H | 2-Furyl | $CH_3$ | (R/S) | |
| 24 | t-Butyl | H | H | 2-Pyridyl | $CH_3$ | (R/S) | |
| 25 | t-Butyl | H | H | 3-Thienyl | $CH_3$ | (R/S) | |
| 26 | t-Butyl | H | H | 2-Benzothienyl | $CH_3$ | (R/S) | 121–122 |
| 27 | 4-Fluorophenyl | H | H | 2-Thienyl | $CH_3$ | (R/S) | 138 |
| 28 | 4-Fluorophenyl | H | H | Phenyl | $CH_3$ | (S) | 169 |
| 29 | 2,4-Difluorophenyl | H | H | Phenyl | $CH_3$ | (S) | 140 |
| 30 | 4-Chlorophenyl | H | H | Phenyl | $CH_3$ | (S) | 195 |
| 31 | 4-Chlorophenyl | H | H | 2-Thienyl | $CH_3$ | (R/S) | 156 |

EXAMPLE 32

Evaluation of the herbicidal activity of compounds of formula I

PLANT SPECIES USED

TRZAW *Triticum aestivum*
HORVW *Hordeum vulgare*
ZEAMX *Zea mays*
GOSHI *Gossypium hirsutum*
GLXMA *Glycine max*
ALOMY *Alopecurus myosuroides*
SETVI *Setaria viridis*
GALAP *Galium aparine*
STEME *Stellaria media*
VERPE *Veronica persica*

IPOHE  *Ipomoea hederacea*
LAMPU  *Lamium purpureum*
PAPRH  *Papaver rhoeas*
MATIN  *Matricaria inodora*
AMARE  *Amaranthus retroflexus*
ABUTH  *Abutilon theophrasti*
AMBEL  *Ambrosia artemisifolia*
CHEAL  *Chenopodium album*

The preemergence tests are conducted by spraying a liquid formulation of the test compound onto the soil in which the seeds of the plant species have recently been sown. The postemergence tests are conducted by spraying a liquid formulation of the test compound onto seedling plants.

The soil used in the tests is a prepared horticultural loam.

The formulations used in the tests are prepared from solutions of the test compound in acetone containing 0.4% by weight of an alkylphenol/ethylene oxide condensate. These acetone solutions are diluted with water and the resulting formulations applied at dosage levels corresponding to 0.8 kg of active material per hectare in a volume equivalent to 900 liters per hectare.

In the preemergence tests untreated sown soil, and in the postemergence tests untreated soil bearing seedling plants, are used as controls.

The herbicidal effect of the test compounds is evaluated twenty days after treatment and is recorded on a 0–9 scale. A rating of 0 indicates growth equivalent to the untreated control, a rating of 9 indicates complete death.

The results of the tests are shown in Table II below. An asterisk denotes the specified plant species was not treated in the test.

I claim:

1. A compound of formula I

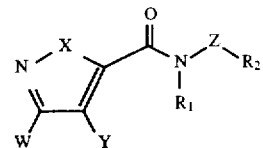

wherein

W represents an optionally substituted alkyl, alkenyl, cycloalkyl, dialkylamino, aryl, heteroaryl or aralkyl group;

Y represents a hydrogen atom; a halogen atom, or an optionally substituted alkyl group;

$R_1$ represents a hydrogen atom, an optionally substituted alkyl group, or an optionally substituted acyl group;

Z represents an $C_{1-4}$ alkylene group being optionally substiuted by a group selected from halogen atoms, and phenyl, nitro, hydroxyl, $C_{1-4}$ alkoxy, $C_{1-4}$ alkyl, $C_{1-4}$ haloalkoxy, ($C_{1-4}$ alkoxy) carbonyl groups, amino, alkyl- and phenyl-sulphinyl, -sulphenyl and -sulphonyl groups, and mono- or di($C_{1-4}$alkyl) amino groups; and $R_2$ represents an aryl or heteroaryl group being optionally substituted by a group selected from halogen atoms, and nitro, cyano, amino, $C_{1-4}$ alkyl, $C_{1-4}$ haloalkyl, $C_{1-4}$ alkoxy and $C_{1-4}$ haloalkoxy groups;

with the proviso that when Z represents an unsubstituted methylene group, then $R_2$ does not represent an unsubstituted phenyl group; or the N-oxides thereof; or the optical isomers thereof.

TABLE II

Herbicidal Evaluation of Test Compounds at 0.8 kg/ha

| Ex. No. | Appl. Time | TRZAW | HORVW | ZEAMX | GOSHI | GLXHA | ALOMY | SETVI | GALAP | STEME |
|---|---|---|---|---|---|---|---|---|---|---|
| 1 | pre | 0 | 0 | 2 | 0 | * | 7 | 8 | 6 | 9 |
|   | post | 4 | 5 | 2 | 8 | 8 | 5 | 9 | 9 | 9 |
| 2 | pre | * | * | * | * | * | * | * | * | * |
|   | post | 3 | 6 | 0 | 9 | 9 | 9 | 9 | 3 | 9 |
| 3 | pre | 0 | 0 | 0 | 0 | 0 | 0 | 0 | 0 | 0 |
|   | post | 0 | 0 | * | 2 | 2 | 0 | 0 | 3 | 4 |
| 4 | pre | 0 | 0 | 2 | 0 | 2 | 5 | 8 | 0 | 9 |
|   | post | 4 | 5 | 5 | 9 | 9 | 7 | 9 | 8 | 9 |
| 5 | pre | 0 | 0 | 0 | 0 | 0 | 0 | 0 | 0 | 1 |
|   | post | 0 | 0 | 0 | 4 | 0 | 0 | 0 | 0 | 4 |
| 6 | pre | 0 | 0 | 0 | 0 | 0 | 0 | 0 | 0 | 4 |
|   | post | 0 | 0 | 3 | 5 | 4 | 3 | 9 | 5 | 9 |

| Ex. No. | Appl. Time | VERPE | IPOHE | LAMPU | PAPRH | MATIN | AMARE | ABUTH | AMBEL | CHEAL |
|---|---|---|---|---|---|---|---|---|---|---|
| 1 | pre | 9 | 3 | 8 | 9 | 9 | 9 | 9 | 8 | 8 |
|   | post | 9 | 9 | 9 | 9 | 9 | 9 | 9 | 8 | 8 |
| 2 | pre | * | * | * | * | * | * | * | * | * |
|   | post | 9 | 9 | 5 | 9 | 9 | * | 9 | 8 | 9 |
| 3 | pre | 0 | 0 | 0 | * | 0 | 7 | 0 | 0 | 0 |
|   | post | 0 | 2 | 3 | 5 | 2 | 4 | 3 | 1 | 6 |
| 4 | pre | 9 | 1 | 6 | 9 | 9 | 7 | 9 | 8 | 8 |
|   | post | 9 | 9 | 6 | 9 | 9 | 7 | 9 | 8 | 9 |
| 5 | pre | 6 | 0 | 0 | 9 | 4 | 4 | 0 | 0 | 4 |
|   | post | 0 | 0 | 3 | 4 | 0 | 6 | 4 | 0 | 2 |
| 6 | pre | 4 | 0 | 4 | 9 | 5 | 7 | 0 | 0 | 3 |
|   | post | 7 | 6 | 4 | 7 | 5 | 9 | 8 | 6 | 7 |

2. The compound according to claim 1, wherein W represents an optionally substituted alkyl alkenyl, cycloalkyl, dialkylamino, phenyl, pyridyl, furyl or thienyl group.

3. The compound according to claim 1 wherein W represents a branched $C_3-C_6$alkyl group or a phenyl group optionally substituted with one or two substituents independently selected from halogen, $C_1-C_4$alkyl, $C_1-C_4$alkoxy and $C_1-C_4$haloalkyl.

4. The compound according to claim 1 wherein Y represents a hydrogen atom.

5. The compound according to claim 1 wherein $R_1$ represents a hydrogen atom.

6. The compound according to claim 1 wherein Z represents —$CH(R_3)$—; and $R_3$ represents a hydrogen atom or an optionally substituted $C_1-C_2$alkyl group.

7. The compound according to claim 1 wherein $R_2$ represents furyl, pyridyl, thienyl, benzothienyl, or phenyl optionally substituted by one or two substituents independently selected from halogen and $C_1-C_4$alkyl.

8. The compound according to claim 1 wherein W represents t-butyl or phenyl; Z represents —$CH(CH_3)$—; and $R_2$ represents phenyl or thienyl.

9. The compound according to claim 1 wherein the optically active isomer is the (S)-isomer.

10. The compound according to claim 1 selected from the group consisting of
(S)-3-t-butyl-isoxazole-5-carboxylic acid (1-phenylethyl)amide;
(S)-3-t-butyl-isoxazole-5-carboxylic acid (1-thien-2-ylethyl)amide;
(R/S)-3-t-butyl-isoxazole-5-carboxylic acid (1-thien-2-ylethyl)amide;
(S)-3-phenyl-isoxazole-5-carboxylic acid (1-phenylethyl)amide;
(R/S)-3-phenyl-isoxazole-5-carboxylic acid (1-thien-2-ylethyl)amide;
(R/S)-3-styryl-isoxazole-5-carboxylic acid (1-thien-2-ylethyl)amide;
(R/S)-3-cyclohexyl-isoxazole-5-carboxylic acid (1-thien-2-ylethyl)amide;
(R/S)-3-dimethylamino-isoxazole-5-carboxylic acid (1-thien-2-ylethyl)amide;
(R/S)-3-(2'-pyridyl)isoxazole-5-carboxylic acid (1-thien-2-ylethyl)amide;
(R/S)-3-(2'-thienyl)isoxazole-5-carboxylic acid (1-thien-2-ylethyl)amide;
(R/S)-3-(4'-methylphenyl)isoxazole-5-carboxylic acid (1-thien-2-ylethyl)amide;
(R/S)-3-(4'-methoxyphenyl)isoxazole-5-carboxylic acid (1-thien-2-ylethyl)amide;
(R/S)-3-(2',4'-difluorophenyl)isoxazole-5-carboxylic acid (1-thien-2-ylethyl)amide;
(R/S)-3-benzyl-isoxazole-5-carboxylic acid (1-thien-2-ylethyl)amide;
(R/S)-3-t-butyl-4-chloro-isoxazole-5-carboxylic acid (1-thien-2-ylethyl)amide;
(R/S)-3-t-butyl-4-methyl-isoxazole-5-carboxylic acid (1-thien-2-ylethyl)amide;
(R/S)-3-t-butyl-isoxazole-5-carboxylic acid N-methyl,N-(1-thien-2-ylethyl)amide;
(R/S)-3-t-butyl-isoxazole-5-carboxylic acid N-acetyl,N-(1-thien-2-ylethyl)amide;
3-t-butyl-isoxazole-5-carboxylic acid (thien-2-yl-methyl)amide;
(R/S)-3-t-butyl-isoxazole-5-carboxylic acid (1-(4'-chlorophenyl)ethyl)amide;
(R/S)-3-t-butyl-isoxazole-5-carboxylic acid (1-(4'-methylphenyl)ethyl)amide;
(R/S)-3-t-butyl-isoxazole-5-carboxylic acid (1-furan-2-ylethyl)amide;
(R/S)-3-t-butyl-isoxazole-5-carboxylic acid (1-(2'-pyridyl)ethyl)amide;
(R/S)-3-t-butyl-isoxazole-5-carboxylic acid (1-thien-3-ylethyl)amide; and
(R/S)-3-t-butyl-isoxazole-5-carboxylic acid (1-(2'-benzothienyl)ethyl)amide.

11. A method for the control of undesirable monocotyledenous and dicotyledenous annual, perennial and aquatic plant species which comprises applying to the foliage of the plants or to the soil or water containing seeds or other propagating organs thereof a herbicidally effective amount of a compound of formula I

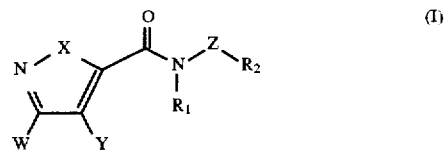
(I)

wherein X represents an oxygen atom;
W represents an optionally substituted alkyl, alkenyl, cycloalkyl, dialkylamino, aryl, heteroaryl or aralkyl group;
Y represents a hydrogen atom, a halogen atom, or an optionally substituted alkyl group;
$R_1$ represents a hydrogen atom, an optionally substituted alkyl group, or an optionally substituted acyl group;
Z represents an optionally substituted $C_1-C_4$alkylene group; and
$R_2$ represents an optionally substituted aryl or heteroaryl group; as defined in claim 1 or
the N-oxides thereof; or
the optical isomers thereof.

12. The method according to claim 11 having a formula I compound wherein W represents an optionally substituted alkyl, alkenyl, cycloalkyl, dialkylamino, phenyl, pyridyl, furyl or thienyl group; Y represents a hydrogen atom; Z represents a —$CH(R_3)$— group; and $R_3$ represents a hydrogen atom or an optionally substituted $C_1-C_2$alkyl group.

13. The method according to claim 11 wherein said undesirable plant species are controlled in the presence of a crop.

14. The method according to claim 13 wherein the crop is a cereal crop or a leguminous crop.

15. The method according to claim 14 wherein the crop is wheat, barley, oat or corn.

16. The method according to claim 11 wherein the formula I compound is applied at a rate of about 0.01 kg/ha to 10 kg/ha.

17. A herbicidal composition which comprises a solid or liquid carrier and a herbicidally effective amount of a compound of formula I

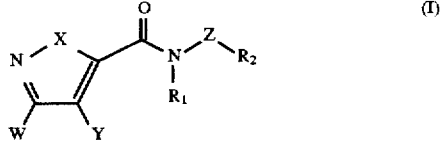
(I)

wherein W, X, Y, Z, $R_1$ and $R_2$ are as defined in claim 11.

18. The herbicidal composition according to claim 17 which comprises at least two carriers at least one of which is a surface-active agent.

19. The herbicidal composition according to claim 17 having a formula I compound wherein W represents an optionally substituted alkyl, alkenyl, cycloalkyl, dialkylamino, phenyl, pyridyl, furyl or thienyl group; Y represents a hydrogen atom; Z represents a —CH(R$_3$)— group; and R$_3$ represents a hydrogen atom or an optionally substituted C$_1$–C$_2$alkyl group.

20. A process for the preparation of a compound of formula I which comprises reacting a compound of formula II

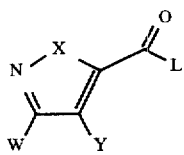
(II)

wherein W, X and Y are as defined in claim 11 and L represents a leaving group, with a compound of formula III or IV

(III)

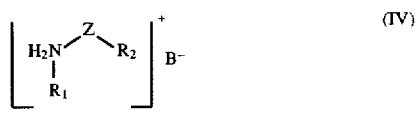
(IV)

wherein Z, R$_1$ and R$_2$ are as defined in claim 11 and B$^-$ is an anion.

* * * * *

UNITED STATES PATENT AND TRADEMARK OFFICE
CERTIFICATE OF CORRECTION

PATENT NO. : 5,780,393

DATED : July 14, 1998

INVENTOR(S) : Trevor W. Newton

It is certified that error appears in the above-identified patent and that said Letters Patent is hereby corrected as shown below:

Column 12, line 3, change the "X" in the chemical formula to "O."

Signed and Sealed this

Twenty-fifth Day of May, 1999

Attest:

Q. TODD DICKINSON

*Attesting Officer*  *Acting Commissioner of Patents and Trademarks*